(12) United States Patent
Pedrozo

(10) Patent No.: US 8,496,642 B2
(45) Date of Patent: Jul. 30, 2013

(54) DEVICE AND METHOD FOR FABRICATING CELLULARIZED IMPLANTS WITH A PREDETERMINED ARCHITECTURE AT THE POINT OF CARE

(75) Inventor: Hugo Antonio Pedrozo, Austin, TX (US)

(73) Assignee: Ortho Biomedical, LLC, Austin, TX (US)

( * ) Notice: Subject to any disclaimer, the term of this patent is extended or adjusted under 35 U.S.C. 154(b) by 0 days.

(21) Appl. No.: 12/821,810

(22) Filed: Jun. 23, 2010

(65) Prior Publication Data

US 2011/0040278 A1 Feb. 17, 2011

Related U.S. Application Data

(60) Provisional application No. 61/219,678, filed on Jun. 23, 2009.

(51) Int. Cl.
*A61M 31/00* (2006.01)
(52) U.S. Cl.
USPC .......................................................... 604/500

(58) Field of Classification Search
USPC .................... 604/500, 264, 263, 265, 288.01, 604/288.04, 93.01; 623/15.12, 23.72
See application file for complete search history.

(56) References Cited

U.S. PATENT DOCUMENTS

| 2010/0042213 A1* | 2/2010 | Nebosky et al. ........... 623/16.11 |
| 2010/0222802 A1* | 9/2010 | Gillespie et al. .............. 606/192 |

* cited by examiner

*Primary Examiner* — Kevin C Sirmons
*Assistant Examiner* — Imani Hayman
(74) *Attorney, Agent, or Firm* — Meyertons, Hood, Kivlin, Kowert & Goetzel, P.C.; Eric B. Meyertons

(57) ABSTRACT

In some embodiments, a method of repairing damaged tissue may include an implant system and method for preparing and using the implant. In some embodiments, a method of repairing damaged tissue may include injecting a first portion of biological material through a first opening in fluid communication with a first end of at least two first channels. In some embodiments, the method may include injecting a second portion of biological material through a third opening in fluid communication with a first end of a sheath. At least a portion of the first channels may be positionable in at least a portion of the sheath. The method may include coupling at least a portion of the sheath and/or at least a portion of at least one of the first channels to at least a portion of a damaged tissue in a human.

20 Claims, 5 Drawing Sheets

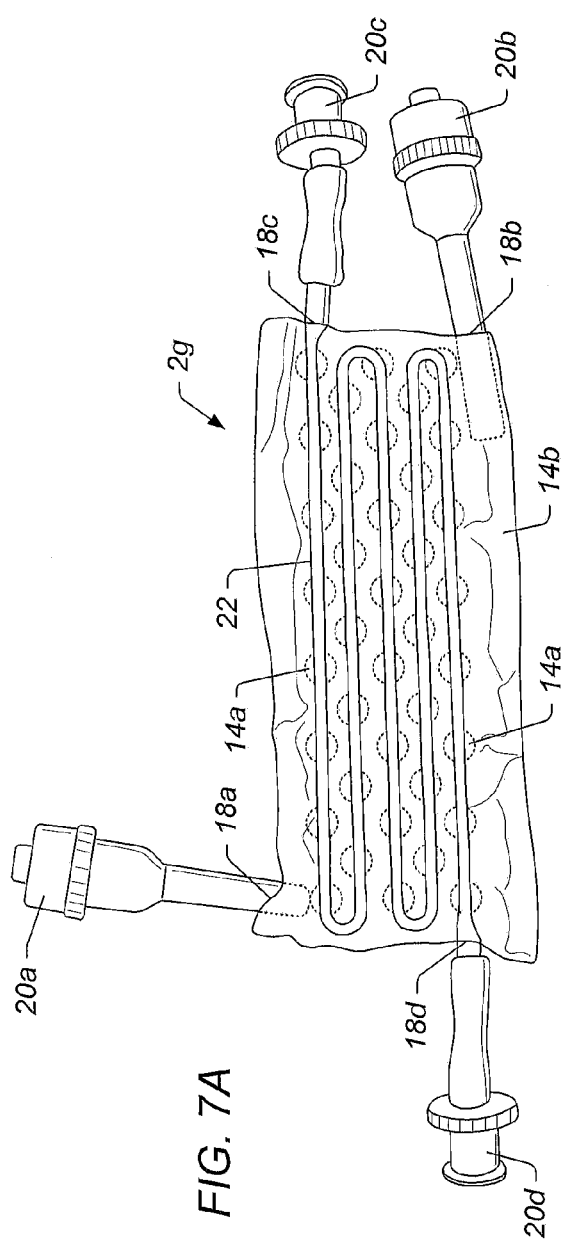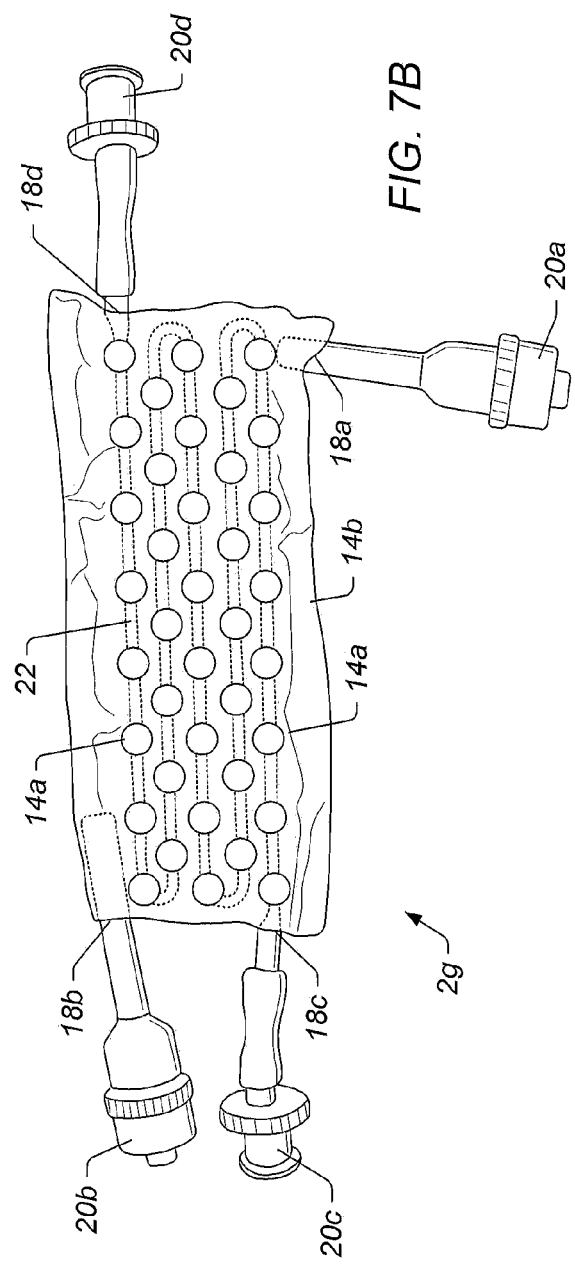
FIG. 7A
FIG. 7B

DEVICE AND METHOD FOR FABRICATING CELLULARIZED IMPLANTS WITH A PREDETERMINED ARCHITECTURE AT THE POINT OF CARE

PRIORITY CLAIM

This application is a claims priority to U.S. Provisional Patent Application No. 61/219,678 entitled "DEVICE AND METHOD FOR FABRICATING CELLULARIZED IMPLANTS WITH A PREDETERMINED ARCHITECTURE AT THE POINT OF CARE" filed on Jun. 23, 2009, all of which is incorporated by reference herein.

BACKGROUND OF THE INVENTION

1. Field of the Invention

The present disclosure generally relates to medical systems and methods for repairing biological tissue. More particularly, the disclosure generally relates to a system and method for an implant system for repairing damaged tissue.

2. Description of the Relevant Art

The field of medical implants has resulted in the development of biocompatible scaffolds with for use in the repair of tissue. For example, the use of porous mesh plugs formed from hydroxy acid polymers has been used for healing bone imperfections. Implants have been described which are both biodegradable and bioresorbable templates. Scaffolds have been produced using vacuum foaming techniques. Implant requiring strength and rigidity (e.g., bone implants) have been formed from metals (e.g., stainless steel, titanium, titanium alloy, nickel, cobalt alloy), composite materials (e.g., composites of carbon, thermosetting resins) and ceramics (e.g., alumina, zirconia, hydroxyapatite). Problems still remain unsolved when using many of these materials: corrosion and fatigue for metals; low toughness and excessively high rigidity for ceramics; and interface destruction for composite materials of inorganic materials with organic polymer materials.

Other types of implants have been formed open cell porous biocompatible foams. Open cell porous biocompatible foams are recognized to have significant potential for use in the repair and regeneration of tissue. Early efforts in tissue repair focused on the use of biocompatible foam as porous plugs to fill voids in bone. An open cell foam of polyhydroxy acids with pores for the in-growth of blood vessels and cells have been previously described. The described foams have been reinforced with fibers, yarns, braids, knitted fabrics, scrims and the like. Unfortunately porous biocompatible foams have several inherent limitations. Foam implants are not easily loaded with biocompatible materials such that the materials are evenly distributed. Foams typically have to soak up the biological material and/or have the material injected directly into the foam implant. It is a difficult and/or time consuming process to evenly distribute biological material throughout many foam implants. This may be problematic during a surgical procedure where time is critical. In some instances foam implants may be pliable much like a sponge, which can cause problems with biological materials injected in the foam implant being expelled when a load is placed on implant compressing it. The biological materials may be expelled prematurely and/or to quickly in such an instance. Foam implants can be limited in the particle size of the biological material which can be loaded into the implant. In addition, when loads are applied to foam based implants, the latter collapse, disintegrate, and in may instances undergo significant plastic deformation, which prevents these loads from being communicated to the cells throughout all layers of the foam material.

Therefore, it is desirable to provide a biocompatible, bioabsorbable implant that provides a continuous gradient of morphological, structural and/or materials. Further, it is preferred that implant materials used in tissue engineering have a structure that provides a template that facilitates the retention of the majority of the cells infused, injected or applied and that are capable of transferring directional deformational loads to the cells which contributes to the proliferation and differentiation of cells, ultimately resulting in the regeneration of functional tissue.

SUMMARY

For the reasons stated above and more, it is desirable to develop an implant system and method for repairing damaged human tissue. In some embodiments, a method of repairing damaged tissue may include injecting a first portion of biological material through a first opening in fluid communication with a first end of at least two first channels. The method may include coupling at least a portion of at least one of the first channels to at least a portion of a damaged tissue in a human.

In some embodiments, the method may include injecting a second portion of biological material through a third opening in fluid communication with a first end of a sheath. At least a portion of the first channels may be positionable in at least a portion of the sheath. The method may include coupling at least a portion of the sheath and/or at least a portion of at least one of the first channels to at least a portion of a damaged tissue in a human.

In some embodiments, a method may include drawing at least some of the injected first portion of biological material through at least one of the first channels towards a second opening in fluid communication with a second end of at least one of the first channels. The method may include drawing at least some of the injected second portion of biological material through the sheath towards a fourth opening in fluid communication with a second end of the sheath. In some embodiments, an implant system may include a syringe coupling mechanism. The syringe coupling mechanism may facilitate standardized syringes to couple to the implant such that biological materials may be injected into containers within the implant.

In some embodiments, the space defined by the inner surface of the sheath and the channels is empty, void of solids and fluids, other than air. In some embodiments, the space defined by the inner surface of the sheath and the channels is filled with a preformed solid matrix composed of resorbable biological or synthetic materials. The solid material may serve as a scaffold for cell spreading and migration from the initial channels where the cells were first injected.

In some embodiments, at least 50% of at least one of the first channels are filled with the first portion of biological material within 30 seconds or less. In some embodiments, at least 50% of the sheath is filled with the second portion of biological material within 30 seconds or less In some embodiments, at least some of the biological material in the first portion is different than the second portion. The biological material may include autologous agents. Autologous agents may include debrided tissue containing differentiated cells and extracelluar matrix components, blood, blood fractions, cells, plasma, growth factors, PRP, marrow, marrow fractions or components thereof. At least some of the biological material may include allogeneic agents. Allogeneic agents may include cells, growth factors, extracellular proteins, agents produced by cultures of mammalian cells, or components thereof. At least some of the biological material may include pharmacological agents. Pharmacological agents may include small molecules recombinant proteins, drugs, or synthetic molecules, or components thereof. At least some of the biological material may include xenogeneic agents. Xenogeneic agents may include cells, hyaluronic acid, collagen, elastin, fibrinogen, growth factors, small molecules, or components thereof.

Tissue may include aggregate of similar cells and cell products forming a definite kind of structural material with a specific function, in a multicellular organism. Examples of tissue which implant systems are used to repair may include cartilage, spinal, ligament, vascular, and/or organ tissue.

In some embodiments, a method may include adjusting at least a portion of the sheath and/or at least a portion of at least one of the first channels to conform to a shape of at least a portion of damaged tissue.

In some embodiments, a method may include inhibiting biological material from prematurely exiting from the sheath and/or at least one of the first channels upon application of a load to the sheath and/or at least one of the first channels.

BRIEF DESCRIPTION OF THE DRAWINGS

Advantages of the present invention may become apparent to those skilled in the art with the benefit of the following detailed description of the preferred embodiments and upon reference to the accompanying drawings.

FIGS. 7A-B depict an embodiment of an implant system sheet with a plurality of first containers positioned in a second container.

Figure 1:
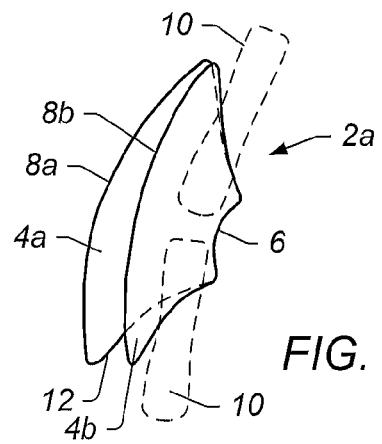
FIG. 1 depicts an embodiment of an implant system with two members coupled together along one edge.

While the invention is susceptible to various modifications and alternative forms, specific embodiments thereof are shown by way of example in the drawing and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION

It is to be understood the present invention is not limited to particular devices, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

Definitions

Unless defined otherwise, all technical and scientific terms used herein have the same meaning as commonly understood by one of ordinary skill in the art.

The term "biodegradable" as used herein generally refers to a material which pieces which degrades within a subject within a discernable period of time (e.g., within months or years).

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The term "distal" as used herein generally refers to a point positioned furthest to a point of reference. The point of reference in the herein described application may be opening of a subject from whence a biological sample is collected and system for collecting biological samples is positioned to collect said sample.

The term "proximal" as used herein generally refers to a point positioned nearer to a point of reference. The point of reference in the herein described application may be opening of a subject from whence a biological sample is collected and system for collecting biological samples is positioned to collect said sample.

The term "tissue" as used herein generally refers to an aggregate of similar cells and cell products forming a definite kind of structural material with a specific function, in a multicellular organism.

In some embodiments, a system and/or method for repairing a portion of human tissue may include an implant system. An implant system may include a number of different containers. Containers may function to inhibit the release of materials positioned in one or more of the containers. An implant system may function to couple two or more pieces of tissue that were previously connected but have been severed due to traumatic injury or disease. An implant system may function to reinforce a portion of tissue which has been weakened or damaged due to traumatic injury, disease, or degeneration.

In some embodiments, it is preferred that implant materials used in tissue engineering have a structure that provides a template that retains cells and facilitates cellular dispersion throughout, proliferation, and differentiation that will ultimately result in regeneration of functional tissue.

An implant system may include one, two or more, or a plurality of containers. Different containers within an implant system may have different sizes and/or shapes.

Medical applications for implant systems described herein may include, but are not limited to, repair of bone (e.g., spine), spinal discs, cartilage (e.g., articular cartilage, meniscus), fibrocartilage, tendons, ligaments, dura, skin, cardiovascular (e.g., vascular grafts, aneurysms, clotted arteries (e.g., creating bypass connectors), neurological (e.g., nerves), and organs (e.g., liver, pancreas). An implant system may be produced in a variety of shapes and sizes depending upon how it is used. Non-absorbable materials may be used to form at least a portion of an implant system for damaged tissue that require more permanent treatment and long-term durability and/or strength. Absorbable materials may be used to form at least a portion of an implant system for tissue defects that require temporary treatment when one wants to avoid the potential complications associated with a permanent implant.

An implant system may be produced in different forms or shapes to facilitate its use depending on the tissue injury to be repaired. A non-limiting example is an implant system with a curvature to construct a substantially cylindrical shape (e.g., a ring shape) and/or an elongated coiling shape. An implant system may be initially formed of a rigid material such that the implant retains the shape with which it is formed. At least a portion of the implant system may be formed of a shape retaining material. For example, a channel may be formed from a flexible polymer, but also include a rigid or semi-rigid elongated member running along a surface of or within the wall of the channel. The elongated member may give the channel its shape.

In some embodiments, a shape of an implant system may be imposed at least in part by the design and not simply a choice of materials. For example, an implant may include two or more channels, the ends of which are coupled to the same points of the implant (e.g., two openings, one at either end of the implant). At least one of the channels may have a longer length relative to one or more of the other channels. The longer channel may have a greater length than the distance between the two openings to which the longer channel is coupled. This extra length of the longer channel may be distorted to into a designed shape, giving the implant an overall different shape mimicking the shape of at least a portion of damaged tissue.

In some embodiments, at least a portion of an implant system may be formed from thermosensitive plastics to enable the cell-implant constructs to change shape in response to heat. Some of these may include multiblock copolymers of polyethylene glycol (PEG), polypropylene oxide, PLGA, PLA, polycaprolactone, and similar polymers.

In some embodiments, at least a portion of an implant system may be formed from so-called shape memory alloys. Shape memory alloys tend to have a temperature induced phase change which will cause the material to have a preferred configuration. The preferred configuration may be fixed by heating the material above a certain transition temperature to induce a change in the phase of the material. When the alloy is cooled back down, the alloy will "remember" the shape it was in during the heat treatment. The alloy will tend to assume the configuration it was in during the heat treatment unless constrained from so doing.

Suitable alloys, including shape memory alloys, may be selected from a group including a cobalt-based low thermal expansion alloy (ELGELOY), nickel-based high temperature high-strength "superalloys" (e.g., nitinol, commercially available from, for example, Haynes International under the trade name HASTELLOY), nickel-based heat treatable alloys (INCOLOY, by International Nickel), and/or a number of different grades of stainless steel.

One or more portions of an implant may include markings that enable the movement and position of the patch to be post-operatively observed and analyzed under imaging systems, such as Magnetic Resonance Imaging ("MRI"), x-ray machines, fluoroscopy or other external visualization methods, for post-operative clinical evaluation. In some embodiments, one or more portions of an implant system may include radiopaque markings. Radiopaque markings may be positioned in a pattern that allows them to be viewed and analyzed during surgery and/or postoperatively. The radiopaque markings may have a shape that matches the area to be repaired and/or reinforced.

Radiopaque markings are made from materials that are impenetrable to radiation (e.g., x-rays). Radiopaque markings may be applied in a variety of methods. For example, if the sheath is from a woven material, then radiopaque threads could be woven into the fabric at specific intervals. Radiopaque threads may be metal (e.g., alloys of gold, nitinol, platinum, or stainless steel). Radiopaque threads could also be made of a biocompatible polymeric material mixed with a metal powder (e.g., barium sulfate). Radiopaque markings could also be imprinted onto the woven material with radiopaque ink.

Other techniques for marking an implant system may include chemical vapor deposition, physical vapor deposition, electroplating, and ion-beam assisted deposition. In ion-beam assisted deposition, an electron beam evaporator is used to create a vapor of atoms that coats the surface of the material.

The markings may be Positron Emission Tomography ("PET") sensitive by making the markings slightly radioactive. Such markings may only be useful for a relatively short time frame after the procedure because of radioactive decay.

The markings may also be attached to the material by a variety of mechanical means such as sewing or weaving the markings into woven material. Similarly, the markings (e.g., metal threads) may be attached to the material by adhesive means (e.g., as bio-compatible glue).

In some embodiments, markings may be arranged in a pattern that allows post operative evaluation. Examples of patterns may include a series of equally spaced substantially parallel lines, a grid of substantially parallel lines, concentric circles, a series of lines radiating from a single point at, for example, a set angle apart.

In some embodiments, containers in an implant system may be conduits (e.g., channels) to facilitate the transport of nutrients and/or invasion of cells into the implant system. At least some of the channels may be interconnecting. An implant system may include one or more channels. In some embodiments, an implant system may include a single container (e.g., channel). In some embodiments, an implant system may include a plurality of containers (e.g., channels). Some channels may facilitate delivery of agents, compounds or cells into the tissue. Pressure methods (e.g., positive, negative) may be employed to delivery agents, compounds, and/or cells. An implant system with improved dispersion of biological materials throughout the implant system has many advantages. Improvement in dispersion may include dispersing biological material throughout at least a portion of the implant system in a substantially evenly distributed manner throughout the portion. Improvement in dispersion may include facilitating rapid distribution of biological materials throughout at least a portion of the implant system. Rapid distribution of biological materials may assist users of the system during implantation in a subject. For example, the implant need not be prepared before the operation and may be prepared during the surgery just prior to use.

In some embodiments, at least 50%, 75%, or 95% of at least one container (e.g., channel) is filled with a portion of biological material within 60 seconds or less. In some embodiments, at least 50%, 75%, or 95% of at least one container (e.g., channel) is filled with a portion of biological material within 20 seconds or less. In some embodiments, at least 50%, 75%, or 95% of at least one container (e.g., channel) is filled with a portion of biological material within 10 seconds or less.

In some embodiments, an implant system may be formed at least in part from a biocompatible material. The biocompatible material may be biodegradable. The biocompatible material may be thermosensitive. Biocompatible materials may be at least partially absorbable by the body. Biocompatible materials may include an absorbable polymer or copolymer (e.g., polyglycolic acid (PGA), polylactic acid (PLA), polycaprolactone, polyhydroxyalkanoate, polyfumarate, polyethylene glycol, polypropylene oxide).

In some embodiments, a biocompatible material may be nonabsorbable. Nonabsorbable biocompatible materials may include polypropylene, polyethylene terephthalate, polytetrafluoroethylene, polyaryletherketone, nylon, fluorinated ethylene propylene, polybutester, and/or silicone.

Implant systems may include biological materials (e.g., collagen, fibrin, elastin). Biological materials such as these may be incorporated into one or more portions of an implant system. Biological materials may be incorporated in the implant system as a component, a coating, and/or may be contained within one or more of the containers within the implant system in soluble, injectable forms, or as pre-formed components of the system.

Implant systems may include materials that inhibit adhesion (e.g., hyaluronic acid). Adhesion inhibition materials may coat a surface of the implant system, reside within one or more of the pores, pathways, or channels, or both. Adhesion inhibition materials may coat an outside surface of an implant system to promote the sliding of the implant against its surrounding tissues (e.g., hand's flexor tendons sliding against the carpal ligament (e.g., carpal tunnel)). Adhesion inhibition materials may degrade as surrounding tissue heals and minimize the risk of future adhesions.

In some embodiment, implant systems may include bioactive coatings or surface treatments which facilitate protein adsorption and/or cell attachment. For example, bioactive peptide sequences (RGD's) may be attached to facilitate protein adsorption and subsequent cell tissue attachment.

In some embodiments, biological materials may include autologous agents. Autologous agents may include blood, cells, cell-extracellular matrix (ECM) fragments, plasma, growth factors, PRP, marrow, or components thereof. Biological materials may include allogeneic agents. Allogeneic agents may include cells, growth factors, extracellular proteins, or components thereof. Biological materials may include pharmacological agents. Pharmacological agents may include small molecules recombinant proteins, drugs, or synthetic molecules, or components thereof. Biological materials may include xenogeneic agents. Xenogeneic agents may include hyaluronic acid, collagen, fibrinogen, growth factors, small molecules, or components thereof. Biological materials may also include naked nucleic acid material, coding elements and gene sequences, viral particles and the like and components thereof.

Biological materials may include one or more proteins (e.g., short chain peptides), chemotatic agents, and/or therapeutic agents (e.g., growth factors, antibiotics, analgesics, anti-inflammatories, anti-rejection (e.g. immunosuppressants) and anticancer drugs), which may be included in the implant system. Biological materials may include one or more types of biological cells (e.g., stem cells, progenitor cells (e.g., osteoblasts), cells of an established cell line, mature cells (e.g., fibroblasts)) or metabolic products of cultured cells (e.g., conditioned media or metabolic products of ex vivo cultures, and fragments thereof). Biological materials may include one or more antibiotics, antiviral agents, or anti-fungal agents, or a combination thereof. Biological materials may include one or more vitamins or minerals. Biological materials may include autograft, allograft, or xenograft bone, bone marrow, adipose tissue, skin fragments, and any other tissues containing pluripotent or multipotent stem cells, and/or morphogenic proteins (BMP's). Biological materials may include osteoinductive or osteoconductive materials.

Biological materials may include growth factors. Growth factors may include cytokines, interleukins, and other peptide growth factors, active fragments, or stimulatory agents produced by cultured cells. Other peptide growth factors may include epidermal growth factor (EGF), members of the fibroblast growth factor (FGF) family, platelet-derived growth factor (PDGF), nerve growth factor (NGF), glial growth factor (GGF), insulin derived growth factor (IGF-I and IGF-II), vascular endothelial growth factor (VEGF), and/or members of the Transforming Growth Factor (TGF) family (e.g., BMPs, Activins, TGF-α or TGF-β) as dimmers monmers, heterodimers, or homodimers.

FIG. 1 depicts an embodiment of implant system 2a with two members 4a and b coupled together along first side 6. In some embodiments, the implant system 2a may be formed from a single member including a crease or fold line which facilitates formation of a channel during use. The implant system may be formed from materials discussed herein. The implant system, for example, may be formed from bioabsorbable polymers with or without porosity.

The implant system 2a depicted in FIG. 1 may be used to couple severed tissue. The implant system 2a depicted in FIG. 1 may be used to repair damaged tissue. A user (e.g., surgeon) during an operation may position two pieces severed or partially severed pieces of tissue (e.g., meniscal tissue or a ligament) between two members 4a and b adjacent first side 6. Second sides 8a and b of members 4a and b may be coupled forming a channel with the damaged tissue positioned inside. Second sides 8a and b may be coupled together such that tissue 10 is inhibited from exiting implant system 2a.

Second sides 8a and b of members 4a and b may be coupled using different methods. For example, the second sides may be coupled using sutures, staples, biocompatible adhesives, or a combination thereof. In some embodiments, the second sides may be heat sealed. In some embodiments, one or more portions of at least one of the members 4a and b may be coupled to tissue 10.

In some embodiments, ends 12 may be sealed around and/or against tissue 10, such that a substantially sealed container is created around the tissue. Biological material may be positioned (e.g., injected) within the created container. The biological materials may facilitate, for example, growth and healing of the damaged tissue. Biological materials may be injected into the created container through the polymer forming members 4a and b. At least a portion of implant forming the container may be formed from a material which is a self-sealing material.

Figure 2:
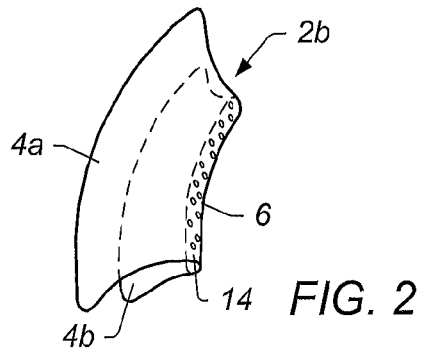
FIG. 2 depicts an embodiment of an implant system with two members coupled together along one edge with a container positioned adjacent the coupled edges.

FIG. 2 depicts an embodiment of implant system 2b with two members 4a and b coupled together along first sides 6 with container 14 positioned adjacent the coupled first sides 6. Implant system 2b may function in a similar manner to implant system 2a in the way the system is implemented to repair damaged tissue. Implant system 2b includes container 14. During use damaged tissue may be positioned adjacent container 14. Container 14 may function to hold biological materials 16. Biological materials may be injected into container 14 through the members 4a and b. At least a portion of the implant forming container 14 may be formed from a material which is a self-sealing material. In some embodiments, implant system 2b may include at least one opening in container 14 through which biological materials may be injected. Implant system 2b may include a syringe coupling mechanism (described herein). The syringe coupling mechanism function to couple to, for example, standard syringes found throughout the medical industry. The syringe coupling mechanism may be coupled via a frangible link, such that after biological materials are injected in container 14 the syringe coupling mechanism may be decoupled from the container.

In some embodiments, container 14 may include a plurality of openings positioned between two members 4a and b. At least some of the openings may function to allow biological material positioned in the container to diffuse through the openings.

In an embodiment, implant system 2b has a curvature along side 6 to better fit the anatomy of the anatomical structure surrounding the implantation site (e.g., the meniscus of the knee or labrum).

Figure 3A:
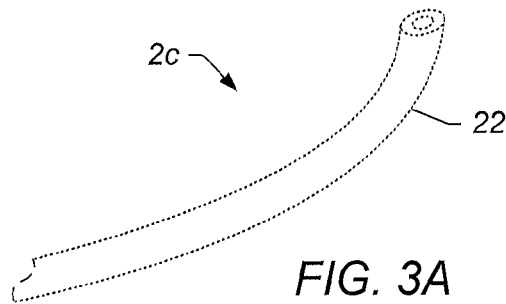
FIGS. 3A-C depict an embodiment of an implant system with an elongated member for delivering biological material.
Figure 3B:
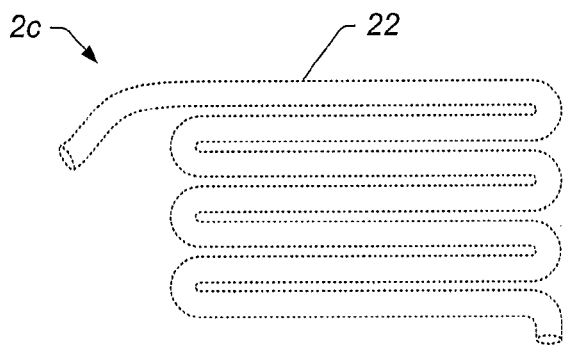
Figure 3C:
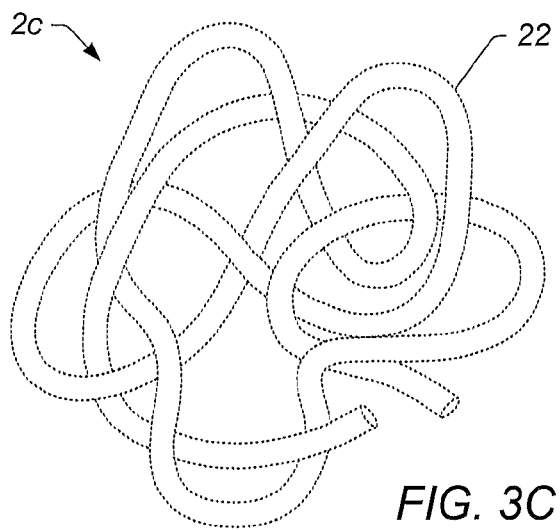

FIGS. 3A-C depict an embodiment of implant system 2c with an elongated member for delivering biological material. The single elongated member may include at least one channel 22.

The channel may be formed from porous materials capable of absorbing biological materials. The channel may include an opening running through at least a majority of the channel. The opening may be used to substantially contain biological materials. The opening may be used to assist positioning the implant system in a subject. The opening may have an elongated guide wire which is positionable in the opening, which when inserted in the opening is used to position the implant in a subject (e.g., through a vascular system).

In some embodiments, implant system 2c may include a first channel positioned in a second channel. Biological materials may be positioned in a void between the outer surface of the first channel and the inner surface of the second channel.

Implant system 2c may be deployed in a subject through the subject's vascular system. The implant system may be deployed to an aneurysm or other vascular defect for endovascular surgical repair. As depicted in FIGS. 3B-C, once the implant system has reached the destination in the subject, the implant system may be compacted into the aneurysm to fill the void and promote the growth of tissue to assist the aneurysm to heal.

Figure 4:
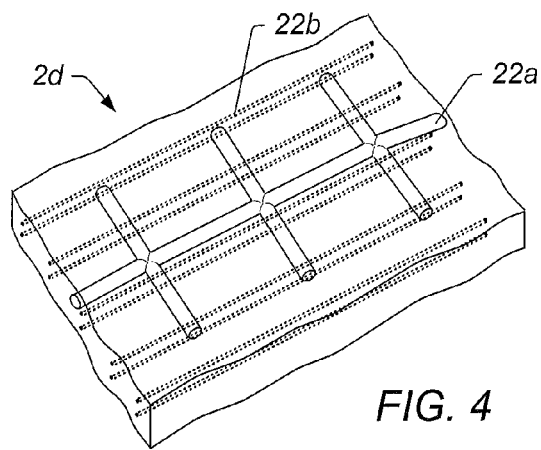
FIG. 4 depicts an embodiment of an implant system formed from a bioabsorbable foam with a plurality of preformed channels.

FIG. 4 depicts an embodiment of implant system 2d formed from a foam with a plurality of preformed channels 22. The foam body of the implant system may be formed into a desired shape by positioning the uncured starting material in a mold. The mold may include elongated members positioned in a desired pattern. When the foam body of the implant has been cured the elongated members may be removed from such that channels 22 are formed throughout the foam body of the implant. At least some of channels 22 may be interconnected. Biological materials may be positioned in channels 22. The foam body itself may be formed from a porous material capable of absorbing one or more different biological materials. The foam body may absorb different biological materials than what is positioned in the channels of the foam body. For example, larger tissue and/or bone fragments may be positioned in at least some of channels 22a, while substantially liquid biological materials (and/or suspensions) may be injected into a different set of channels (e.g., relatively smaller channels 22b) to be absorbed into the foam body (and/or the foam body may be positioned in the liquid biological material (e.g., blood, growth hormones)).

In some embodiments, a foam body of implant system 2d may be positioned in a second container (e.g., sheath 24). Sheath 24 may function to prevent biological materials from being prematurely expelled when a load is applied to implant system 2d. Sheath 24 may be formed from bioabsorbable materials. Sheath 24 may be formed from substantially porous materials (which may still inhibit premature expelling of biological materials positioned in the foam body of the implant system).

Figure 5:
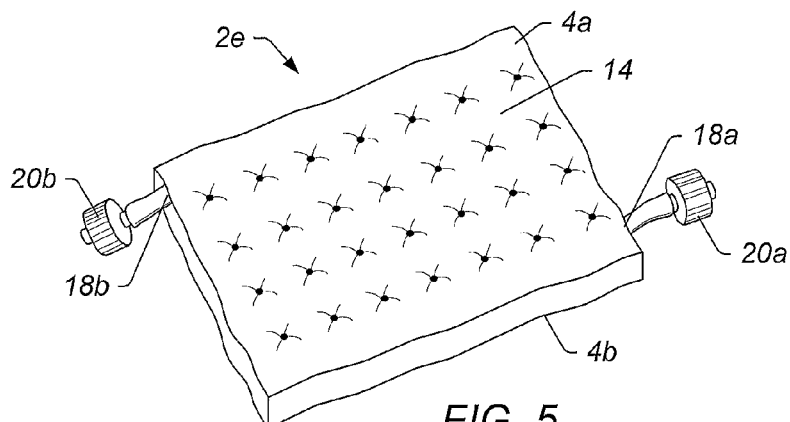
FIG. 5 depicts an embodiment of an implant system with two members stitched together in discrete and alternating points.

FIG. 5 depicts an embodiment of implant system 2e with two members 4a and b coupled together at various points. Two members 4a and b may be coupled together along the perimeter forming container 14. In some embodiments, two members 4a and b may be coupled together in discrete and alternating points. The two members may be coupled together to inhibit movement of the members relative to one another. This inhibition of relative movement may encourage substantially equivalent distribution of biological materials positioned between members 4a and b. Part and/or all of implant system 2e may formed from bioabsorbable and/or porous materials.

In some embodiments, implant system 2e may include a system for efficiently delivering biological materials quickly to container 14. Container 14 may include first opening 18a and second opening 18b. First opening 18a and second opening 18b may be in fluid communication with container 14. The embodiment depicted in FIG. 5 includes syringe coupling mechanisms 20a and b. Syringe coupling mechanisms 20a and b may be in fluid communication with first opening 18a and second opening 18b respectively. A syringe containing biological material may be coupled to syringe coupling mechanism 20a, and biological material may be injected through first opening 18a in container 14. Second opening 18b may allow fluids (e.g., air) already contained in container 14 to escape as the injecting biological material replaces the fluids. The second opening then functions to expedite loading of the biological material into the container. In some embodiments, a second unloaded syringe may be coupled to syringe coupling mechanism 20b. The second unloaded syringe may be used to create a negative pressure (e.g., by withdrawing existing fluids in the container) in the container to further expedite loading of biological material in the container. Syringe coupling mechanisms 20a and/or b may be decoupled after biological materials have been injected in the container. Opening 18 may substantially seal after decoupling syringe coupling mechanism 20.

Figure 6:
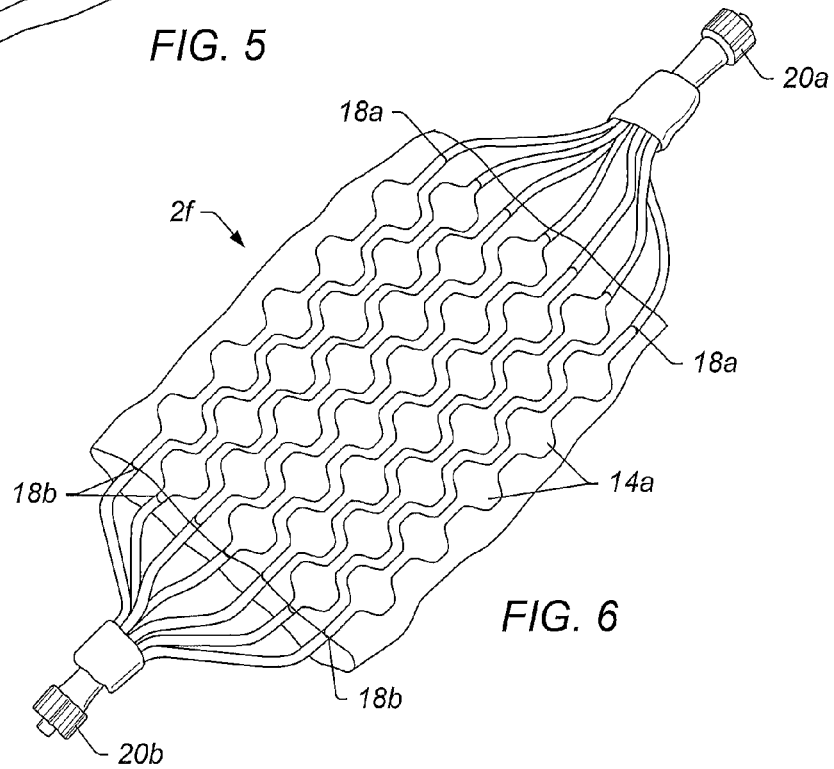
FIG. 6 depicts an embodiment of an implant system with a plurality of first containers.

FIG. 6 depicts an embodiment of implant system 2f with a plurality of first containers 14a. The embodiment depicted in FIG. 6 may be used to for cartilage repair or tendon (rotator cuff) repair, or tissue fillers. A body of implant system 2f may include a plurality of first containers 14a. The plurality of containers may function to hold biological materials. The containers may be voids or space in the body of the implant in fluid communication with at least some of the other containers in the implant.

In some embodiments, implant system 2f may include a system for efficiently delivering biological materials quickly to container 14. Containers 14 may include first openings 18a and second openings 18b. First openings 18a and second openings 18b may be in fluid communication with containers 14. The embodiment depicted in FIG. 6 includes syringe coupling mechanisms 20a and b. Syringe coupling mechanisms 20a and b may be in fluid communication with first openings 18a and second openings 18b respectively. A syringe containing biological material may be coupled to syringe coupling mechanism 20a, and biological material may be injected through first openings 18a in containers 14. Second openings 18b may allow fluids (e.g., air) already contained in containers 14 to escape as the injecting biological material replaces the fluids. The second openings then function to expedite loading of the biological material into the containers. In some embodiments, a second unloaded syringe may be coupled to syringe coupling mechanism 20b. The second unloaded syringe may be used to create a negative pressure (e.g., by withdrawing existing fluids in the containers) in the containers to further expedite loading of biological material in the containers. Syringe coupling mechanisms 20a and/or b may be decoupled after biological materials have been injected in the container. Opening 18 may substantially seal and/or include a mechanism to seal them after decoupling syringe coupling mechanism 20.

FIGS. 7A-B depict an embodiment of implant system 2g with a plurality of first containers 14a positioned in second container 14b. First containers 14a may be used to contain a first portion of biological materials. Second containers 14a may be used to contain a second portion of biological materials. First containers 14a may be coupled to at least one inner surface of second container 14b. First containers 14a may be coupled to two inner surfaces of second container 14b. In some embodiments, one or more sides of first containers 14a may be formed from second container 14b. Coupling first containers 14a to second container 14b may function to inhibit movement of first containers 14a relative to second container 14b Inhibiting movement of first containers 14a relative to second container 14b may help ensure that biological materials held within first containers 14a are distributed throughout second container 14b in a desired manner (e.g., substantially evenly distributed).

In some embodiments, implant system 2g may include a system for efficiently delivering biological materials quickly to the plurality of first containers 14a and second container 14b. Second container 14b may include first opening 18a and second opening 18b. First opening 18a and second opening 18b may be in fluid communication with second container 14b. The embodiment depicted in FIG. 7 includes syringe coupling mechanisms 20a and b. Syringe coupling mechanisms 20a and b may be in fluid communication with first opening 18a and second opening 18b respectively. A syringe containing biological material may be coupled to syringe coupling mechanism 20a, and biological material may be injected through first opening 18a in second container 14b. Second opening 18b may allow fluids (e.g., air) already contained in second container 14b to escape as the injecting biological material replaces the fluids. The second opening then functions to expedite loading of the biological material into the second container. In some embodiments, a second unloaded syringe may be coupled to syringe coupling mechanism 20b. The second unloaded syringe may be used to create a negative pressure (e.g., by withdrawing existing fluids in the second container) in the second container to further expedite loading of biological material in the second container.

Implant system 2g may include a one or more channels 22. Channels 22 may be in fluid communication with first containers 14a. Channels 22 may include third opening 18c and fourth opening 18d. Third opening 18c and fourth opening 18d may be in fluid communication with channels 22. The embodiment depicted in FIG. 7 includes syringe coupling mechanisms 20c and 20d. Syringe coupling mechanisms 20c and d may be in fluid communication with third opening 18c and fourth opening 18d respectively. A syringe containing biological material may be coupled to syringe coupling mechanism 20c, and biological material may be injected through third opening 18c in first containers 14a. Fourth opening 18d may allow fluids (e.g., air) already contained in first containers 14a to escape as the injecting biological material replaces the fluids. The fourth opening then functions to expedite loading of the biological material into the first container. In some embodiments, a second unloaded syringe may be coupled to syringe coupling mechanism 20d. The second unloaded syringe may be used to create a negative pressure (e.g., by withdrawing existing fluids in the first containers) in the first containers to further expedite loading of biological material in the first containers.

In some embodiments, channels 22 and/or syringe coupling mechanisms 20 may be decouplable from first containers 14a and/or second container 14b. The channels and/or the syringe coupling mechanisms may be removed before the implant system is coupled to human tissue. The channels and/or the syringe coupling mechanisms may be removed after the desired biological materials are positioned in the first and/or second containers. In some embodiments, the first and/or second containers may be formed at least in part from a self-sealing material, such that when the channels and/or the syringe coupling mechanisms are decoupled biological materials in the first and/or second containers are inhibited from prematurely exiting.

Figure 8:
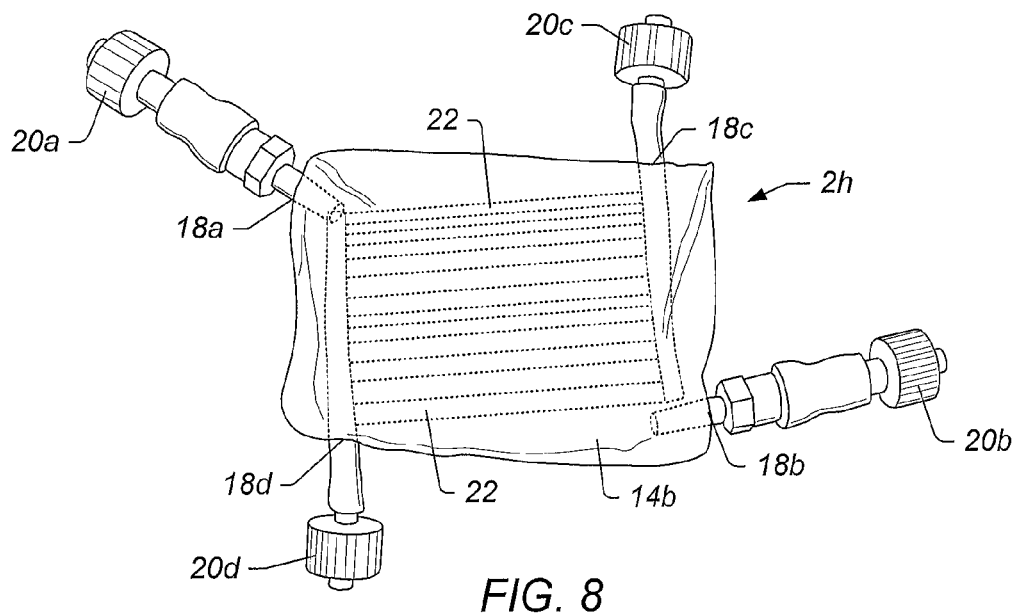
FIG. 8 depicts an embodiment of an implant system with a plurality of elongated members positioned in a sheath.

FIG. 8 depicts an embodiment of implant system 2h with a plurality of channels 22 positioned in a second container 14b. In the embodiment depicted in FIG. 8, channels 22 are functioning as the first containers. In some embodiments, implant system 2h may include a system for efficiently delivering biological materials quickly to the plurality of channels 22 and second container 14b. The system may function in a similar manner to the embodiment depicted in FIG. 7. Second container 14b may include first opening 18a and second opening 18b. First opening 18a and second opening 18b may be in fluid communication with second container 14b. Syringe coupling mechanisms 20a and b may be in fluid communication with first opening 18a and second opening 18b respectively.

A syringe containing biological material may be coupled to syringe coupling mechanism 20a, and biological material may be injected through first opening 18a in second container 14b. Second opening 18b may allow fluids (e.g., air) already contained in second container 14b to escape as the injecting biological material replaces the fluids. The second opening then functions to expedite loading of the biological material into the second container. In some embodiments, a second unloaded syringe may be coupled to syringe coupling mechanism 20b. The second unloaded syringe may be used to create a negative pressure (e.g., by withdrawing existing fluids in the second container) in the second container to further expedite loading of biological material in the second container.

Channels 22 may include third opening 18c and fourth opening 18d. Third opening 18c and fourth opening 18d may be in fluid communication with channels 22. Syringe coupling mechanisms 20c and d may be in fluid communication with third opening 18c and fourth opening 18d respectively. A syringe containing biological material may be coupled to syringe coupling mechanism 20c, and biological material may be injected through third opening 18c into channels 22. Fourth opening 18d may allow fluids (e.g., air) already contained in channels 22 to escape as the injecting biological material replaces the fluids. The fourth opening then functions to expedite loading of the biological material into the channels. In some embodiments, a second unloaded syringe may be coupled to syringe coupling mechanism 20d. The second unloaded syringe may be used to create a negative pressure (e.g., by withdrawing existing fluids in the channels) in the first containers to further expedite loading of biological material in the channels.

Figure 9:
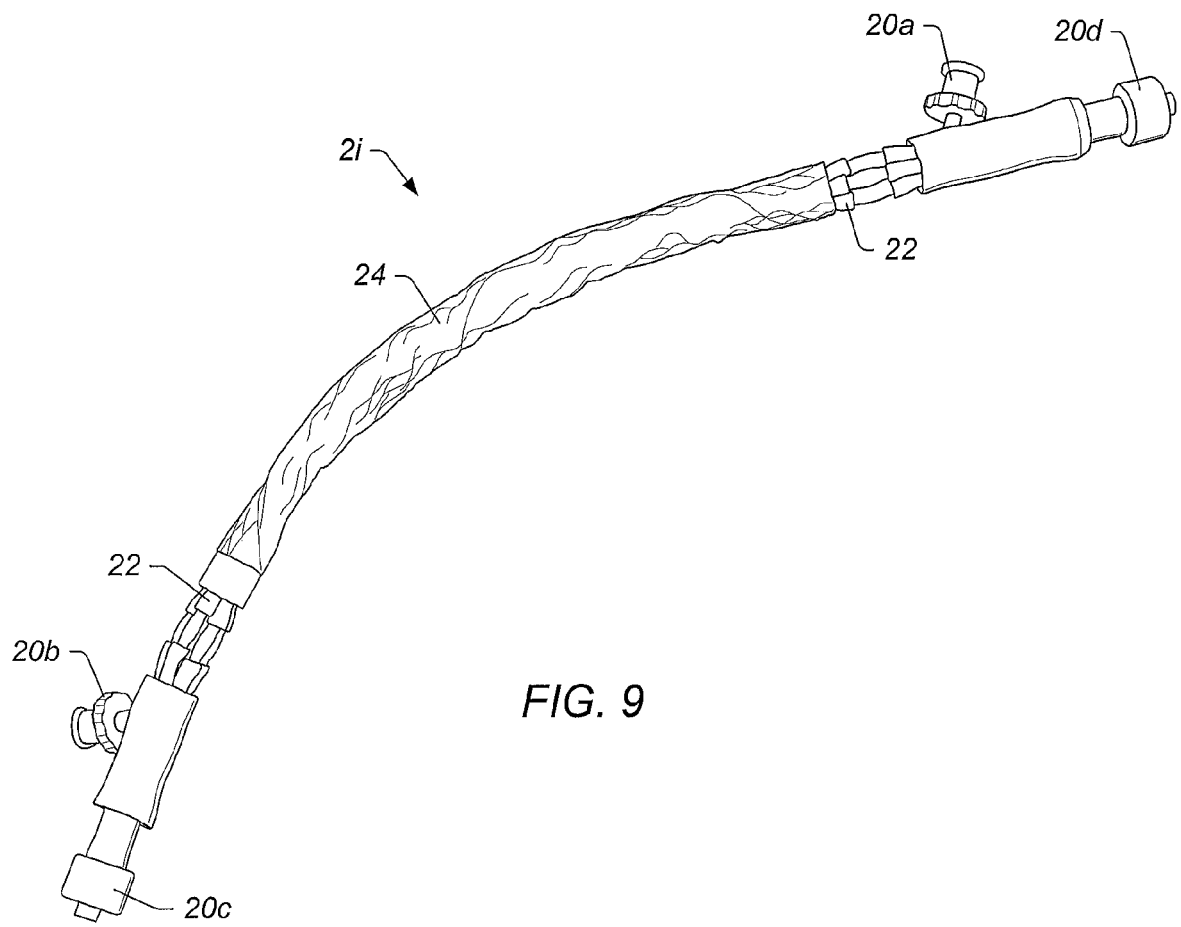
FIG. 9 depicts an embodiment of an implant system with a plurality of elongated members positioned in a sheath.
Figure 10:
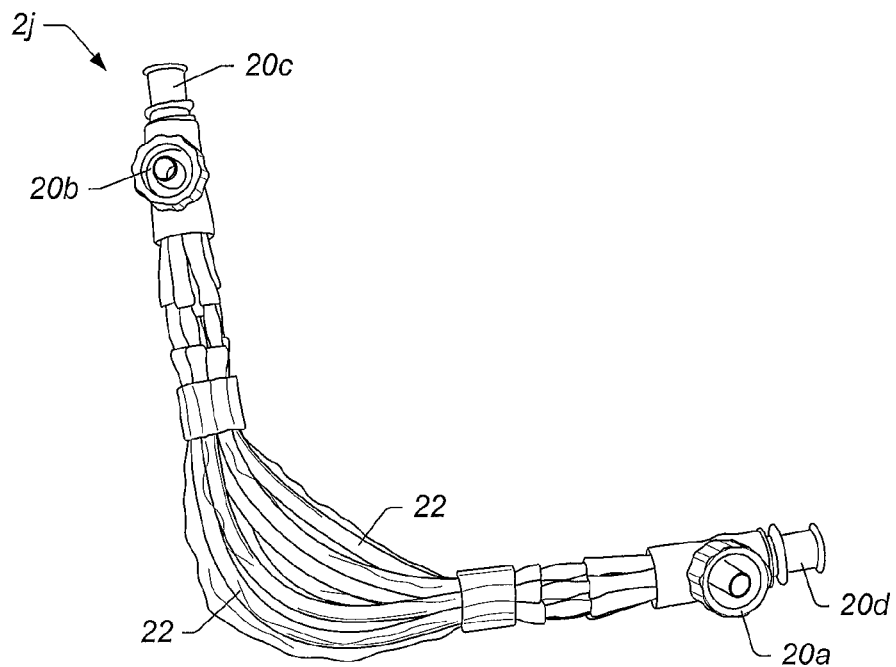
FIG. 10 depicts an embodiment of an implant system with a plurality of elongated members with different lengths and positioned in a sheath.
Figure 11:
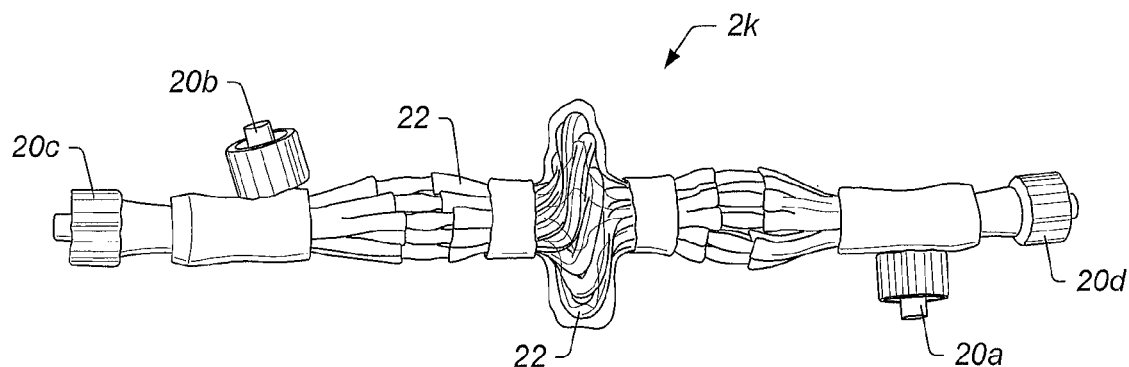
FIG. 11 depicts an embodiment of an implant system with a plurality of elongated members positioned in a sheath configured for a spinal implant.

FIGS. 9-11 depict embodiments of implant systems 2i-k with plurality of channels 22 positioned in sheath 24. In the embodiment depicted in FIGS. 9-11, channels 22 are functioning as the first containers. In the embodiment depicted in FIG. 9, sheath 24 is functioning as the second container. In some embodiments, implant systems 2i-k may include a system for efficiently delivering biological materials quickly to the plurality of channels 22 and sheath 24. The system may function in a similar manner to the embodiment depicted in FIG. 7. Sheath 24 may include first opening 18a and second opening 18b. First opening 18a and second opening 18b may be in fluid communication with sheath 24. Syringe coupling mechanisms 20a and b may be in fluid communication with first opening 18a and second opening 18b respectively.

A syringe containing biological material may be coupled to syringe coupling mechanism 20a, and biological material may be injected through first opening 18a in sheath 24. Second opening 18b may allow fluids (e.g., air) already contained in sheath 24 to escape as the injecting biological material replaces the fluids. The second opening then functions to expedite loading of the biological material into the sheath. In some embodiments, a second unloaded syringe may be coupled to syringe coupling mechanism 20b. The second unloaded syringe may be used to create a negative pressure (e.g., by withdrawing existing fluids in the sheath) in the sheath to further expedite loading of biological material in the sheath.

Channels 22 may include third opening 18c and fourth opening 18d. Third opening 18c and fourth opening 18d may be in fluid communication with channels 22. Syringe coupling mechanisms 20c and d may be in fluid communication with third opening 18c and fourth opening 18d respectively. A syringe containing biological material may be coupled to syringe coupling mechanism 20c, and biological material may be injected through third opening 18c into channels 22. Fourth opening 18d may allow fluids (e.g., air) already contained in channels 22 to escape as the injecting biological material replaces the fluids. The fourth opening then functions to expedite loading of the biological material into the channels. In some embodiments, a second unloaded syringe may be coupled to syringe coupling mechanism 20d. The second unloaded syringe may be used to create a negative pressure (e.g., by withdrawing existing fluids in the channels) in the first containers to further expedite loading of biological material in the channels.

In some embodiments, a shape of an implant system may be imposed at least in part by the design and not simply a choice of materials. For example, an implant may include two or more channels, the ends of which are coupled to the same points of the implant (e.g., two openings, one at either end of the implant). At least one of the channels may have a longer length relative to one or more of the other channels. The longer channel may have a greater length than the distance between the two openings to which the longer channel is coupled. This extra length of the longer channel may be distorted to into a designed shape, giving the implant an overall different shape mimicking the shape of at least a portion of damaged tissue. FIGS. 10-11 depict embodiments of implant systems 2j-k with plurality of channels 22 positioned in sheath 24 (the sheathes are not depicted in the embodiments in FIGS. 10-11). In the embodiments depicted in FIGS. 10-11, one or more channels 22 may be shorter in length relative to the other channels which results in the relatively longer channels assuming a nonlinear shape.

In some embodiments, a single implant may result from the combination of two or more systems described herein. For instance, a new system results from the combination of systems described in FIG. 6 plus FIGS. 1 and 2, or the system in FIG. 4 plus FIG. 1 or 2, or the system described in FIG. 5 in the center of the implant surrounded by the system in FIG. 1 or 2, or both, in the periphery.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of repairing damaged tissue in a human, comprising:
    obtaining a tissue repair system comprising at least two containers and a sheath, wherein at least a portion of the at least two containers are disposed in at least a portion of the sheath;
    injecting a first portion of biological material through a first opening in fluid communication with a first end of the at least two containers, wherein the containers are substantially sealed after injection of the biological material through the first opening;
    injecting a second portion of biological material through a third opening in fluid communication with a first end of a sheath, wherein the second portion of biological material is disposed in the sheath surrounding at least a portion of the at least two containers; and
    coupling at least a portion of the tissue repair system to at least a portion of a damaged tissue in a human.

2. The method of claim 1, wherein the first portion of biological material is different than the second portion of biological material.

3. The method of claim 1, wherein at least a portion of at least one of the channels and/or at least a portion of the sheath is substantially bioabsorbable when implanted in a human.

4. The method of claim 1, wherein at least 50% of at least one of the containers is filled with the first portion of biological material within 30 seconds or less.

5. The method of claim 1, further comprising adjusting at least a portion of the sheath and/or at least a portion of the containers to conform to a shape of at least a portion of the damaged tissue.

6. The method of claim 1, further comprising drawing at least some of the injected first portion of biological material through at least one of the containers towards a second opening in fluid communication with a second end of the containers.

7. The method of claim 1, further comprising drawing at least some of the injected second portion of biological material through the sheath towards a fourth opening in fluid communication with a second end of the sheath.

8. The method of claim 1, further comprising coupling a syringe to a syringe coupling mechanism in fluid communication with the first, second, third, and/or fourth opening.

9. The method of claim 1, wherein the first portion of biological material and/or the second portion of biological material comprises autologous agents.

10. The method of claim 1, wherein the first portion of biological material and/or the second portion of biological material comprises allogeneic agents.

11. The method of claim 1, wherein the first portion of biological material and/or the second portion of biological material comprises pharmacological agents.

12. The method of claim 1, wherein the first portion of biological material and/or the second portion of biological material comprises xenogeneic agents.

13. The method of claim 1, wherein the damaged tissue comprises cartilage tissue.

14. The method of claim 1, wherein the damaged tissue comprises spinal tissue.

15. The method of claim 1, wherein the damaged tissue comprises at least a portion of a ligament.

16. The method of claim 1, wherein the damaged tissue comprises at least a portion of a blood vessel.

17. The method of claim 1, wherein the damaged tissue comprises at least a portion of an organ.

18. An implant system for a human, comprising:
at least two containers, wherein the at least two containers are in fluid communication with a first opening, and wherein the at least two containers are configured to at least partially contain biological material injected into the at least two containers through the first opening, wherein the containers are substantially sealed after injection of the biological material through the first opening; and wherein biological material disposed in the sheath surrounds at least a portion of the at least two containers during use;
a sheath, wherein the at least two containers are positionable in at least a portion of the sheath, wherein the sheath is in fluid communication with a third opening, and wherein the sheath is configured to at least partially contain biological material injected through the third opening.

19. The method of claim 1, wherein the at least two containers comprise a second end, and wherein the second portion of biological material surrounds at least a portion of the container between the first end and the second end.

20. The implant of claim 18, wherein the at least two containers comprise a second end, and wherein the second portion of biological material surrounds at least a portion of the container between the first end and the second end.

* * * * *